(12) United States Patent
Darmos et al.

(10) Patent No.: US 7,318,822 B2
(45) Date of Patent: Jan. 15, 2008

(54) HYBRID CANNULA/ELECTRODE MEDICAL DEVICE AND METHOD

(75) Inventors: George P. Darmos, Willowdale (CA); Ilya Gavrilov, Etobicoke (CA); Peter G. Darmos, Willowdale (CA)

(73) Assignee: Diros Technology Inc., Markham, Ontario (CA)

( * ) Notice: Subject to any disclaimer, the term of this patent is extended or adjusted under 35 U.S.C. 154(b) by 484 days.

(21) Appl. No.: 10/933,245

(22) Filed: Sep. 3, 2004

(65) Prior Publication Data

US 2006/0052850 A1    Mar. 9, 2006

(51) Int. Cl.
*A61B 18/18*    (2006.01)
*A61B 5/00*    (2006.01)

(52) U.S. Cl. .................. 606/31; 607/102; 606/42; 606/45; 600/549

(58) Field of Classification Search .............. 606/31, 606/41, 42, 45–50; 607/102; 600/549
See application file for complete search history.

(56) References Cited

U.S. PATENT DOCUMENTS

| | | | |
|---|---|---|---|
| 4,411,266 A | 10/1983 | Cosman | |
| 4,966,597 A * | 10/1990 | Cosman | 606/50 |
| 5,470,309 A | 11/1995 | Edwards et al. | |
| 5,556,377 A | 9/1996 | Rosen et al. | |
| 5,904,681 A * | 5/1999 | West, Jr. | 606/41 |
| 6,044,846 A | 4/2000 | Edwards | |
| 6,162,216 A | 12/2000 | Guziak et al. | |
| 6,371,926 B1 * | 4/2002 | Thorson et al. | 600/549 |
| 6,391,005 B1 * | 5/2002 | Lum et al. | 604/117 |
| 6,632,221 B1 * | 10/2003 | Edwards et al. | 606/41 |
| 2005/0267552 A1 * | 12/2005 | Conquergood et al. | 607/96 |

FOREIGN PATENT DOCUMENTS

| | | |
|---|---|---|
| WO | WO 97/17105 | 5/1997 |
| WO | WO 99/08613 | 2/1999 |

\* cited by examiner

*Primary Examiner*—Michael Peffley
(74) *Attorney, Agent, or Firm*—Bereskin & Parr

(57) ABSTRACT

A cannula having a hollow metal tube for injection of liquids such as an anesthetic, or RF energy, into a patient. A thermocouple or other temperature sensor is located at the bare tip of the cannula, and a wire for the temperature sensor extends along the length of the cannula, preferably in a groove formed in the tube, or through a passageway formed in the tube. An outer insulation layer covers the tube and wire. Thus, a single device serves as both a cannula and an electrode.

4 Claims, 5 Drawing Sheets

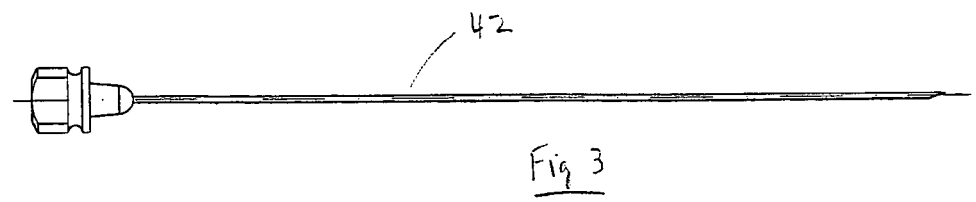
Fig. 3
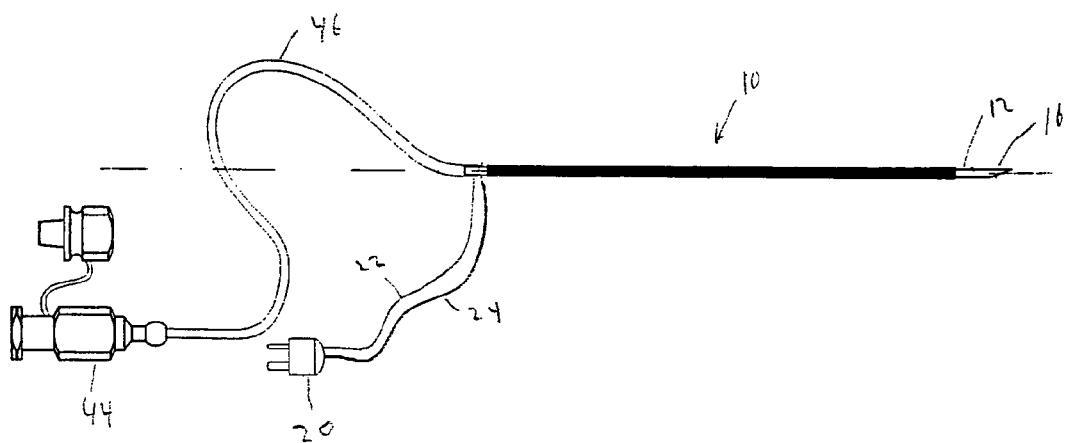
Fig. 4
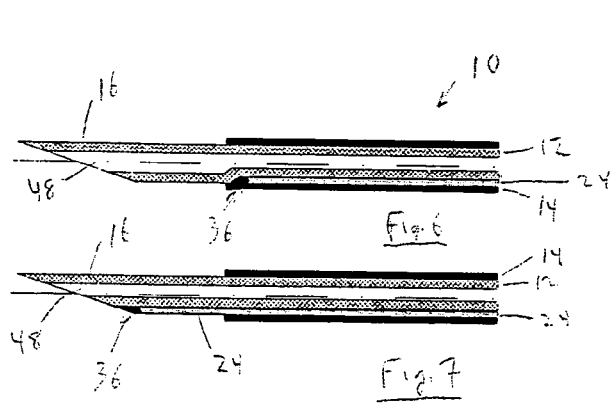
Fig. 6
Fig. 7
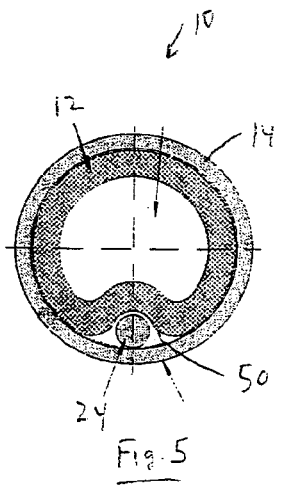
Fig. 5

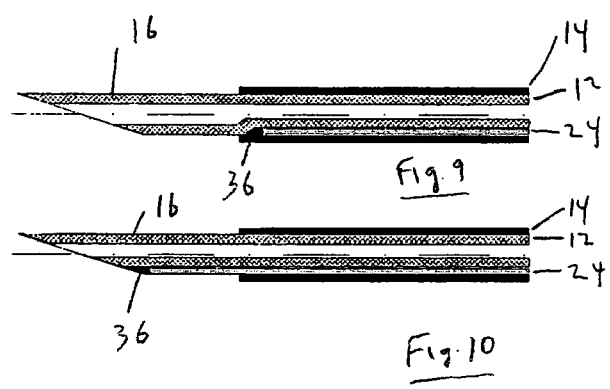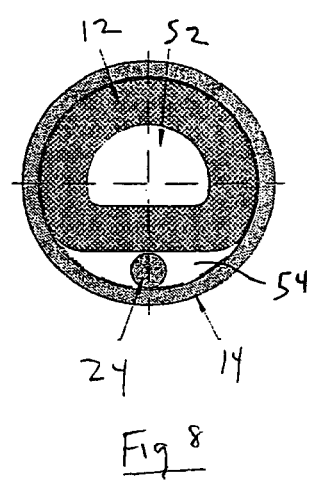

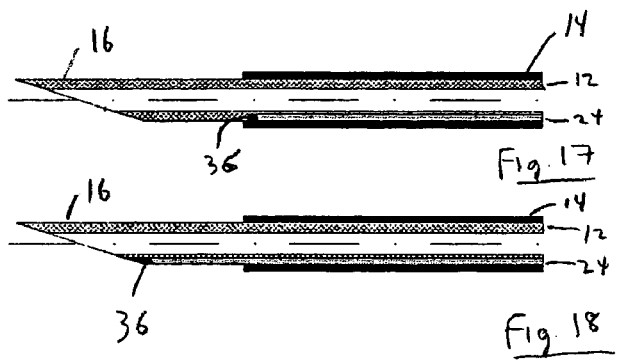
Fig. 17
Fig. 18
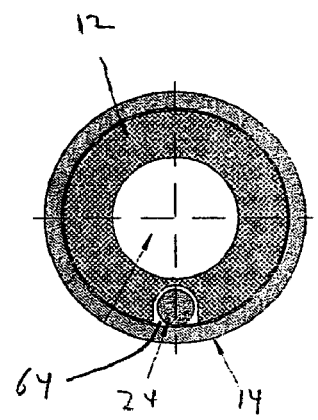
Fig. 16
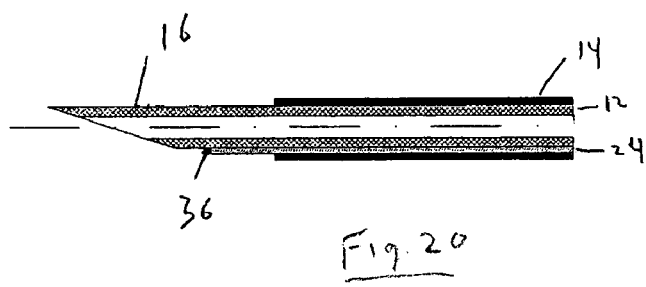
Fig. 20
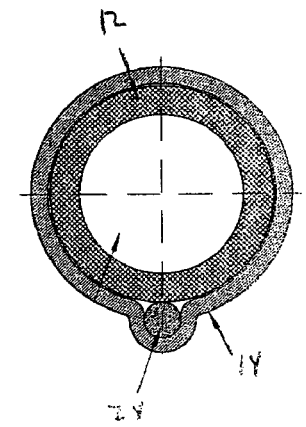
Fig. 19

HYBRID CANNULA/ELECTRODE MEDICAL DEVICE AND METHOD

FIELD OF THE INVENTION

This invention relates to an instrument to be used in medical applications, in which energy (commonly radio frequency energy) is to be emitted in the vicinity of tissue in a patient.

BACKGROUND OF THE INVENTION

Radio frequency (RF) energy is commonly used to treat patients who fail to respond to other methods of treatment. RF treatment can be used in pain management, neurosurgery, cardiac surgery, and in the treatment of cancer. The method involves applying to tissue a radio frequency electric field, using commercially available instruments, such as the OWL RF Lesion Generators manufactured by Diros Technology Inc. of Markham, Ontario, Canada. Both the heat and the electromagnetic field produced can have a biological effect on tissue. The energy can be used to stimulate, ablate or treat tissue.

Usually in RF treatment, electrodes are inserted into an insulated cannula that typically has a sharp, beveled, exposed bare tip so that the cannula may penetrate tissue, enter the body, and be guided (usually using a fluoroscope) toward tissue such as a neural structure or cardiac structure. The same cannula that accepts the electrode can also be used to deliver an anesthetic liquid, or a diagnostic localization agent to the target structure or tissue in the body, but this can only be done when the electrode is not inserted into the cannula. Thus two physical devices are required, one being the electrode structure, and the other being the cannula. The need to purchase, sterilize and use two separate devices adds complexity and cost to surgical procedures.

SUMMARY OF THE INVENTION

Accordingly, it is an object of this invention to provide a single instrument which constitutes both a cannula and also an electrode. This eliminates the need to purchase, sterilize and use two separate devices, thereby simplifying the surgical procedure and reducing cost and potential complications.

In one aspect the invention provides a cannula comprising (a) a hollow metal tube having a base end and a free tip, and an internal passage extending from the base end to the tip, (b) an insulation layer covering a majority of the length of said tube but not covering said tip and thereby leaving said tip exposed, (c) a temperature sensor wire extending along said tube from said base to a position adjacent said tip, said wire being insulated from said tube along the length of said tube but being electrically connected to a temperature sensor adjacent said tip, said temperature sensor also being connected to said tube so that said tube and said wire form two conductors of a circuit for said temperature sensor, (d) said wire being within said insulation layer, so that said cannula can be inserted into a patient and a liquid can be injected through said passage into said patient, and so that RF energy can be applied through said cannula while the temperature adjacent said tip is sensed by said temperature sensor.

In another aspect the invention provides a method of using a cannula, said cannula comprising a hollow metal tube having a base end and a free tip and an internal passage extending from the base end to the tip, an insulation layer covering a majority of the length of said tube but leaving said tip exposed, and a temperature sensor wire extending along said tube from said base to a position adjacent said tip, said wire being insulated from said tube along the length of said tube but being electrically connected to a temperature sensor adjacent said tip, said wire being within said insulation layer, said method comprising inserting said cannula into a patient to place said tip at a desired location within said patient, injecting a liquid such as an anesthetic through said cannula to anesthetize tissue at said location, applying energy through said cannula to said location, and measuring the temperature at said location using said temperature sensor.

Further objects and advantages of the invention will appear from the following description, taken together with the accompanying drawings.

BRIEF DESCRIPTION OF THE DRAWINGS

FIG. 3 is a side view of a stylet for use with a cannula according to the invention;

FIG. 4 is a view similar to that of FIG. 1 but showing the hub attached to a flexible tube which tube is then attached to the cannula;

FIG. 5 is a cross-sectional view of a cannula according to the invention;

FIG. 6 is a longitudinal sectional view of the cannula of FIG. 5;

FIG. 7 is a longitudinal sectional view of a modified cannula according to the invention;

FIG. 8 is a cross-sectional view of another embodiment of a cannula according to the invention;

FIG. 9 is a longitudinal sectional view of the cannula of FIG. 8;

FIG. 10 is a longitudinal sectional view of another embodiment of the cannula of FIGS. 8 and 9;

FIG. 16 is a cross-sectional view of another embodiment of a cannula according to the invention;

FIG. 17 is a longitudinal sectional view of the cannula of FIG. 16;

FIG. 18 is a longitudinal sectional view of another embodiment of the cannula of FIGS. 16 and 17;

FIG. 19 is a cross-sectional view of another embodiment of a cannula according to the invention; and FIG. 20 is a longitudinal sectional view of the cannula of FIG. 19.

DETAILED DESCRIPTION OF THE INVENTION

Figure 1:
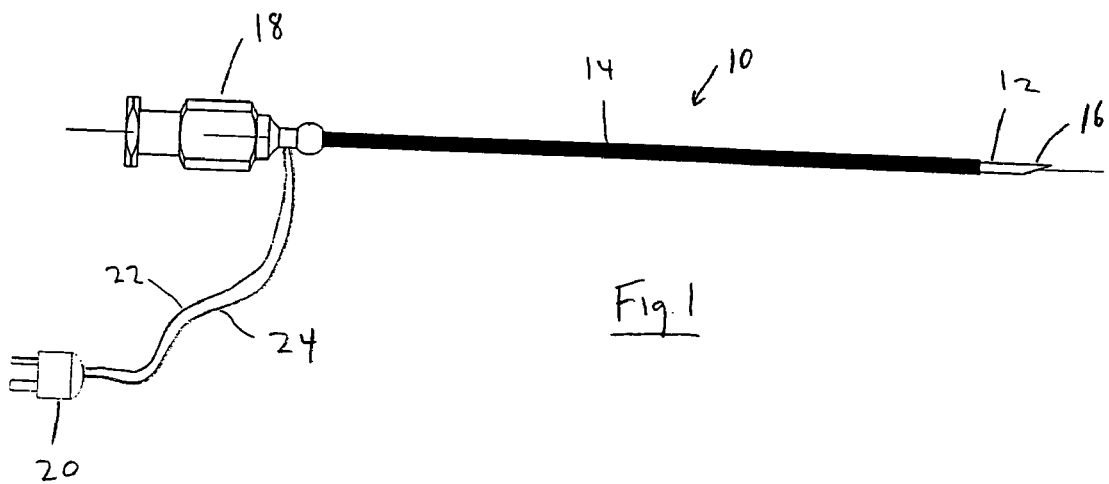
FIG. 1 is an exploded view of apparatus according to the invention, showing a hub attached directly to a cannula.
Figure 2:
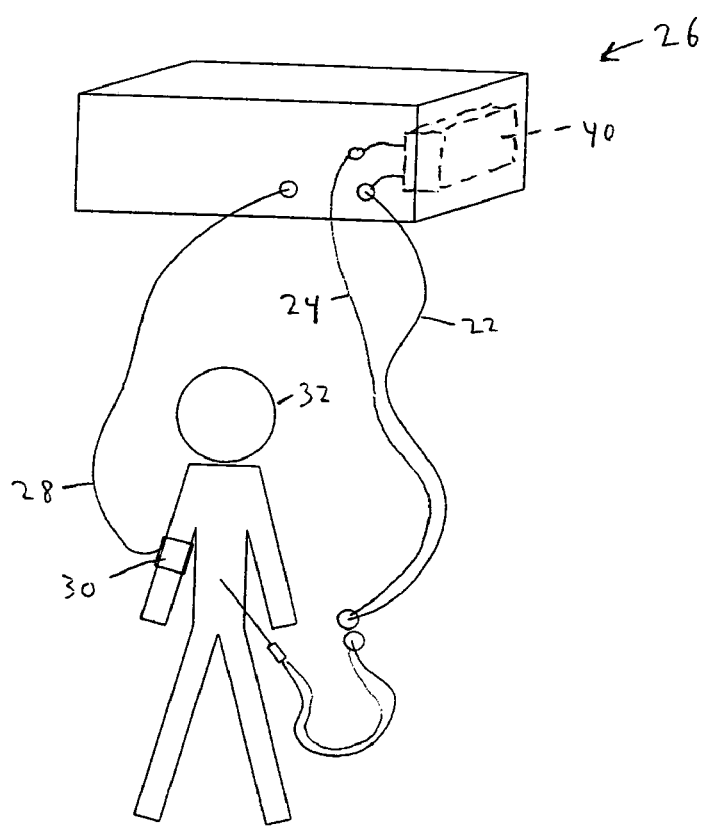
FIG. 2 is a diagrammatic view showing electrical connection of a cannula according to the invention to a patient and to an energy source.

Reference is first made to FIG. 1 and FIG. 2, which show generally an embodiment of the invention. FIG. 1 shows a cannula 10 formed from medical grade tubing 12 such as medical grade stainless steel covered by an insulation layer 14. Insulation layer 14 is normally medical grade insulation such as polyester. The insulation 14 does not cover and thus exposes a polished bare tip 16 at the distal end of the cannula. There is also typically a hub 18 (usually of plastic) mounted to the proximal end of the cannula 10.

The cannula 10 shown in the drawings is capable of receiving energy from an energy source, such as an RF lesion generator, and delivering that energy to the bare tip 16. As shown, an electrical connector 20 is connected by two wires 22, 24 to the cannula 10. One of the wires 22 is electrically connected (e.g. by silver solder or spot welding) to the metal tube 12 adjacent the proximal end of the cannula (but wire 22 can be connected to tube 12 anywhere up to the distal end of the cannula, by running wire 22 under insulation layer 14 in the manner to be described for wire 24.) The wire 22 serves to conduct electrical energy from the energy source such as an RF lesion generator, into the cannula 10. The lesion generator is shown at 26 in FIG. 2, and the other half of the circuit for the RF energy is provided by a further conductor 28 from the lesion generator to a dispersive pad 30 on the patient 32, as shown in FIG. 2.

The second wire 24 from connector 20 serves as part of the temperature sensor circuit. The second wire 24 extends along the length of the cannula in a manner to be described, and as shown in FIGS. 6 and 7, terminates adjacent the bare tip 16 at a hot junction 36. The hot junction 36 consists of the wire 24, which can be copper or constantin, that is electrically connected (by solder or spot welding) to the tube 12, so that the other half of the circuit for the thermocouple is formed by the conductive tube 12 and first wire 22. (If desired, other thermocouple types or a thermistor can be used in place of the thermocouple described.)

Thus, the single device shown is capable of receiving energy from the energy source 26 and delivering that energy to the bare tip 16. It is also capable of relaying temperature information from the bare tip 16 to the energy source controller 40 (part of lesion generator 26) via the wires 22, 24 and connector 20, so that the amount of RF energy applied can be controlled.

The hub 18 can be affixed to the cannula directly, coaxially with the tube 12, as shown in FIG. 1, in which case a stylet 42 (FIG. 3) can be inserted into the hub 18 and through the tube 12 to facilitate penetration of the device into tissue. In addition, an appropriate liquid, such as an anesthetic, can be injected through the hub 18 and through the tube 12 to the tip 16, to anesthetize the area in question before application of RF energy to the bare tip 16. The liquid to be injected can also be an appropriate diagnostic localization agent.

Alternatively, and as shown in FIG. 4, the hub 44 can be separate from the cannula and can be connected to the cannula 10 through a flexible tube 46 (made e.g. of PVC). As before, an anesthetic or diagnostic localization agent can be injected through the hub 44 into the tube 46 (e.g. by a syringe) and delivered through the cannula 10 and the hole 48 at the tip of the cannula, into the patient.

A feature of the invention is that the wire 24 which forms one part of the thermocouple circuit (the other part being the metal tube 12) must extend along the length of the cannula to a location adjacent the bare tip of the cannula, where the thermocouple is located. It will be realized that the thermocouple must be in the "heat envelope" of the exposed tip 16, i.e. within the volume of tissue which is heated when energy is radiated from the cannula tip. According to the invention, there are several preferred arrangements for extending the wire 24 along the length of the cannula.

In one arrangement, shown in FIG. 5, the metal tube 12 (which would normally be circular in cross-section) is provided with a groove 50 in its outer surface. The groove 50 extends along the length of the tube 12 and is of a size sufficient to house the wire 24 (which is insulated from the tube 12). The combination of the tube 12, groove 50 and insulated wire 24 are all covered by the outer layer of insulation 14. The wire 24 terminates at and is joined to the hot junction 36 (which as mentioned consists of a second wire such as copper or constantin, but different from the first wire 24). The hot junction 36 can be located where the insulation layer 14 ends (e.g. just under the insulation), as shown in FIG. 6, or it can be located at the open end of the tip 16, near hole 48, as shown in FIG. 7, or it can be anywhere between these two locations.

A second arrangement is shown in FIGS. 8 to 10, where the metal tubing 12 is D-shaped in cross-section (and the passageway 52 through the tube 12 is also D-shaped in cross-section). The outer layer of insulation 14 is circular in cross-section and is rigid, leaving a space 54 between the insulation 14 and the tube 12. The wire 24 extends through the space 54.

Figure 12:
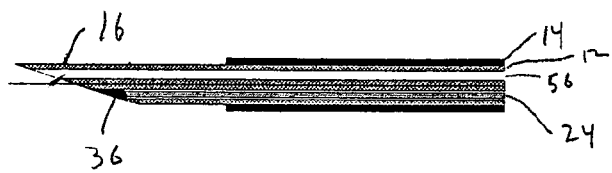
FIG. 12 is a longitudinal sectional view of the cannula of FIG. 11.
Figure 11:
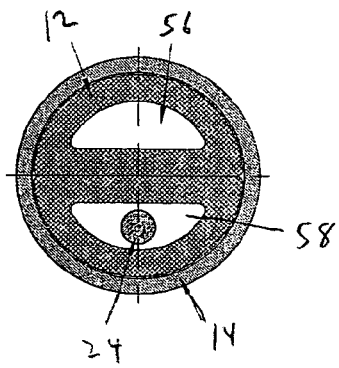
FIG. 11 is a cross-sectional view of another embodiment of a cannula according to the invention.

A further arrangement is shown in FIGS. 11 and 12, where the tube 12 is shown as having a double D-shape in cross-section, providing two D-shaped passageways 56, 58 which extend longitudinally through the full length of the cannula. The first passageway 56 is used for injection of appropriate liquids, such as the anesthetic or diagnostic localization agent mentioned. The second passageway 58 is used to accommodate the insulated thermocouple wire 24, which as shown in FIG. 10 terminates at the open end of the tip 16, where the hot junction 36 is located.

Figure 14:
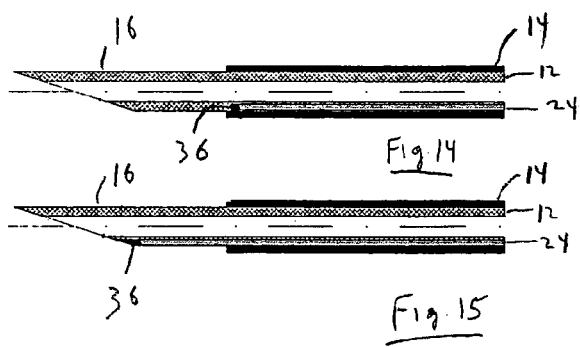
FIG. 14 is a longitudinal sectional view of the cannula of FIG. 13.
Figure 15:
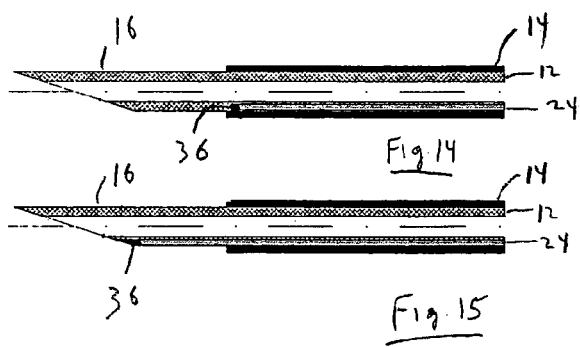
FIG. 15 is a longitudinal sectional view of another embodiment of the cannula of FIGS. 13 and 14.
Figure 13:
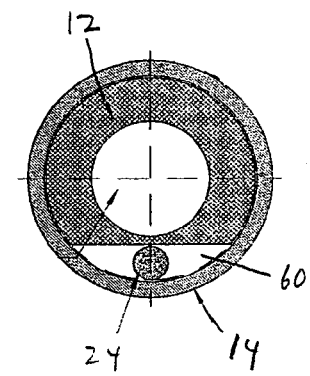
FIG. 13 is a cross-sectional view of another embodiment of a cannula according to the invention.

Another alternative arrangement is shown in FIGS. 13 to 15. This arrangement is similar to the arrangement shown in FIG. 8 except that instead of the tube 12 being D-shaped, a portion of the outer periphery of the tube 12 is ground or machined off, leaving a space 60 between the tube 12 and the outer insulation layer 14. The space 60 accommodates the thermocouple wire 24, which as before is shown as extending to the open end of the tube where it terminates in the hot junction 36 (FIGS. 14, 15).

Yet another arrangement is shown in FIGS. 16 to 18. Here, the tube 12 is circular, but a groove 64 is machined therein to accommodate the thermocouple wire 24. The tube 12, groove 64, and wire 24 are all covered by the outer insulation layer 14. As before, the thermocouple wire 24 extends to the hot junction 36, which as shown in FIG. 18 can be located at the open tip 16 of the cannula, or as shown in FIG. 17 can be located just at the end of the outer insulation layer 14.

Finally, and as shown in FIGS. 19 and 20, the tube 12 can be entirely circular in cross-section, and the wire 24 can be located on the outer periphery of the tube 12 and retained in place by the outer insulation layer 14 which extends over the wire 24. This forms a longitudinally extending "bump" on the exterior of the cannula, which may not be preferred, depending on the application.

While preferred embodiments of the invention have been described, it will be realized that various changes can be made, and these are all intended to be included within the scope of the invention.

The invention claimed is:

1. A cannula comprising: (a) a hollow metal tube having a base end and a free tip, and an internal passage extending from the base end to the tip, (b) an insulation layer covering a majority of the length of said tube but not covering said tip and thereby leaving said tip exposed, (c) a temperature sensor wire extending along said tube from said base to a position adjacent said tip, said wire being insulated from said tube along the length of said tube but being electrically connected to a temperature sensor adjacent said tip, said temperature sensor also being connected to said tube so that said tube and said wire form two conductors of a circuit for said temperature sensor, (d) said wire being within said insulation layer, so that said cannula can be inserted into a patient and a liquid can be injected through said passage into said patient, and so that RF energy can be applied through said cannula while the temperature adjacent said tip is sensed by said temperature sensor, (e) said tube having an outer surface having a crease therein extending longitudinally along said tube, said wire being located in said crease, and said crease and said wire being covered by said insulation layer.

2. A cannula comprising: (a) a hollow metal tube having a base end and a free tip, and an internal passage extending from the base end to the tip, (b) an insulation layer covering a majority of the length of said tube but not covering said tip and thereby leaving said tip exposed, (c) a temperature sensor wire extending along said tube from said base to a position adjacent said tip, said wire being insulated from said tube alone the length of said tube but being electrically connected to a temperature sensor adjacent said tip, said temperature sensor also being connected to said tube so that said tube and said wire form two conductors of a circuit for said temperature sensor, (d) said wire being within said insulation layer, so that said cannula can be inserted into a patient and a liquid can be injected through said passage into said patient, and so that RF energy can be applied through said cannula while the temperature adjacent said tip is sensed by said temperature sensor, (e) said tube being D-shaped in cross-section, having a flat surface extending longitudinally along said tube, said insulation layer covering said flat surface and defining with said flat surface a space therebetween, said wire being located in said space.

3. A cannula comprising: (a) a hollow metal tube having a base end and a free tip, and an internal passage extending from the base end to the tip, (b) an insulation layer covering a majority of the length of said tube but not covering said tip and thereby leaving said tip exposed, (c) a temperature sensor wire extending along said tube from said base to a position adjacent said tip, said wire being insulated from said tube along the length of said tube but being electrically connected to a temperature sensor adjacent said tip, said temperature sensor also being connected to said tube so that said tube and said wire form two conductors of a circuit for said temperature sensor, (d) said wire being within said insulation layer, so that said cannula can be inserted into a patient and a liquid can be injected through said passage into said patient, and so that RF energy can be applied through said cannula while the temperature adjacent said tip is sensed by said temperature sensor, (e) said tube having an outer periphery, said outer periphery being circular in cross-section except for a flat portion extending longitudinally along the length of said tube, said insulation layer defining with said flat surface a space therebetween, said wire being located within said space.

4. A cannula comprising: (a) a hollow metal tube having a base end and a free tip, and an internal passage extending from the base end to the tip, (b) an insulation layer covering a majority of the length of said tube but not covering said tip and thereby leaving said tip exposed, (c) a temperature sensor wire extending alone said tube from said base to a position adjacent said tip, said wire being insulated from said tube along the length of said tube but being electrically connected to a temperature sensor adjacent said tip, said temperature sensor also being connected to said tube so that said tube and said wire form two conductors of a circuit for said temperature sensor, (d) said wire being within said insulation layer, so that said cannula can be inserted into a patient and a liquid can be injected through said passage into said patient, and so that RF energy can be applied through said cannula while the temperature adjacent said tip is sensed by said temperature sensor, (e) said tube has a groove formed therein, said groove extending longitudinally along said tube, said wire being located within said groove, said tube, groove and wire being covered by said insulation layer.

* * * * *